United States Patent
Del Giglio

(10) Patent No.: US 6,200,332 B1
(45) Date of Patent: Mar. 13, 2001

(54) DEVICE AND METHOD FOR UNDERSKIN LASER TREATMENTS

(75) Inventor: Antonio Del Giglio, Verona (IT)

(73) Assignee: CeramOptec Industries, Inc., East Longmeadow, MA (US)

( * ) Notice: Subject to any disclaimer, the term of this patent is extended or adjusted under 35 U.S.C. 154(b) by 0 days.

(21) Appl. No.: 09/351,073

(22) Filed: Jul. 9, 1999

(51) Int. Cl.[7] .................................................. A61N 5/00
(52) U.S. Cl. .............................. 607/89; 607/92; 607/93; 606/9; 606/15; 606/16
(58) Field of Search ........................... 607/88–93; 606/2, 606/7, 9–11, 13–17

(56) References Cited

U.S. PATENT DOCUMENTS

| | | | |
|---|---|---|---|
| 4,846,171 | * | 7/1989 | Kauphusman et al. . |
| 4,895,145 | * | 1/1990 | Joffe et al. . |
| 5,257,989 | * | 11/1993 | Celaya et al. . |
| 5,300,067 | * | 4/1994 | Nakajima et al. . |
| 5,456,681 | * | 10/1995 | Hajjar . |
| 5,531,739 | | 7/1996 | Trelles . |
| 5,578,029 | | 11/1996 | Trelles et al. . |
| 5,766,164 | * | 6/1998 | Mueller et al. . |

OTHER PUBLICATIONS

Kristen M. Kelly et. al., "Cryogen Spray Cooling in Combination with Nonablative Laser Treatment of Facial Rhytides," Arch. Dermatol., 135(1999)691–694.

J. Stuart Nelson, MD, PhD et. al., "Dynamic Epidermal Cooling During Pulsed Laser Treatment of Port–Wine Stain," Arch. Dermatol., 131(1995)695–700.

Bahman Anvari et. al., "A Theoretical Study of the Thermal Response of Skin to Cryogen Spray Cooling and Pulsed Laser Irradiation: Implications For Treatment of Port Wine Stain Birthmarks," Phys. Med. Biol., 40(1995) 1451–1465.

\* cited by examiner

Primary Examiner—Linda C. M. Dvorak
Assistant Examiner—Bryan K. Yarnell
(74) Attorney, Agent, or Firm—Bolesh J. Skutnik; B J Associates

(57) ABSTRACT

A device and method for underskin laser treatment that is minimally invasive, versatile and precise, that allows for underskin laser treatment with only minimal insertions into the area of treatment. For example, an entire area may be treated with one insertion. The device and method incorporates a standard insertion component making the system inexpensive and easy for doctors to use. In addition, the the invention allows users to get in direct contact with the treatment site, eliminating deleterious side effects encountered when treatment is administered to the skin surface. The device and method has applications in several areas of treatment. First, underskin treatment of aesthetic skin blemishes such as sagging and wrinkles can be performed with minimal external effects. Laser power is delivered directly beneath the skin, bypassing harmful exposure of the skin surface to the radiation. Second, common vascular abnormalities such as capillary disorders, spider nevus, hemangioma, and varicose veins can be selectively eliminated. The device allows a simple, single insertion per treated structure and specific laser delivery. The needle is inserted into the vascular structure and any abnormalities are eradicated starting from the source and continuing through the entire structure. Third, when coupled with x-ray imaging, the present invention may be used to treat various internal body structures for example during surgery. X-ray imaging allows the user to orient the device within the body structures. Laser delivery treatment can then be administered as described above.

12 Claims, 2 Drawing Sheets

DEVICE AND METHOD FOR UNDERSKIN LASER TREATMENTS

BACKGROUND OF THE INVENTION

1. Field of the Invention

The invention relates generally to medical laser treatments performed beneath the skin and more specifically to correction of skin disfigurement, to eradication of vascular abnormalities, and to various operations performed on internal body structures.

2. Invention Disclosure Statement

Underskin laser treatment is an effective way to eliminate many abnormalities. A below the skin application provides a more proximal access to the area of treatment enabling the use of a less powerful and less harmful laser. Straight form surface treatments require laser energy to be focused on the skin surface, commonly leading to undesired side effects such as external discoloration or scarring. The present invention describes an underskin laser treatment system that can be utilized for correcting skin irregularities, eradicating vascular abnormalities, and operating in various parts of the body. Radiation administered below the surface of the skin provides a more proximal application with reduced risks of accidentally exposing surrounding tissue to the laser radiation.

Dermatological laser treatments have been reported to cure skin wrinkles. Laser energy is used to selectively trigger the body's normal healing process. Effectively, the lasing induces fibroblast activity resulting in collagen proliferation. The wrinkle is filled in and thereby reduced. The method involves flashing a laser onto the skin surface above the wrinkle to induce underskin effects. The desired area of treatment however lies beneath the skin surface. The laser energy must penetrate the epidermal layer to reach the derma. This distance of the beam from the treatment site and the loss of energy due to reflection of the beam at the skin surface necessitate using a higher power laser. As a result, potential, undesired surface damage occurs. Such damage may include prolonged erythema, scaring, dyspigmentation, and infection. To prevent these side effects, one laser method employs a cryogen spray that is projected onto the epidermis during treatment to counteract the laser heat energy. The cooling part of the process allows users to selectively effect the derma while protecting the overlying layers. The success and safety of the procedure then depends greatly on the consistent application of the coolant. Further, devices needed to dispense the coolant, for example a coolant reservoir on the laser delivery device, makes the invention more complex and potentially more expensive and cumbersome. [See, e.g., Kristen M. Kelly et. al., "Cryogen Spray Cooling in Combination With Nonablative Laser Treatment of Facial Rhytides," *Arch. Dermatol.*, 135 (1999) 691–694., J. Stuart Nelson, M D, PhD et. al., "Dynamic Epidermal Cooling During Pulsed Laser Treatment of Port-Wine Stain," *Arch. Dermatol.*, 131 (1995) 695–700., Bahman Anvari et. al., "A Theoretical Study of the Thermal Response of Skin to Cryogen Spray Cooling and Pulsed Laser Irradiation: Implications For Treatment of Port Wine Stain Birthmarks," *Phys. Med. Biol.*, 40 (1995) 1451–1465.]

The present invention describes an improved method of wrinkle removal. By allowing laser energy to be delivered subcutaneously, the present invention substantially prevents against surface epidermal injury. Further, the closer proximity of the application of the radiation to the underskin site allows a lower power application reducing the amount of deleterious side effects in general.

Laser treatment below the surface of the skin has also been described in U.S. Pat. No. 5,531,739 to Trelles. There a method is described whereby an optical probe is inserted into the skin adjacent to a vascular abnormality. Introducing laser pulses will serve to collapse and close off the vein. This method requires multiple insertions of the device along the desired vein to treat the abnormality. The procedure has limitations. First, the described method is specific for treatment of veins, primarily in the leg, and is therefore limited to that specific treatment. Second, the procedure requires a low power beam to illuminate and direct the probe to the treatment site under the skin. Treatment is then limited to underskin sites at a depth that the illumination beam can penetrate. Third, the method describes delivery of the laser power to the vicinity of, and outside the vein requiring treatment. Such laser treatment closes off the vein by collapsing its wall, an indirect solution.

In addition, U.S. Pat. No. 5,578,029 to Trelles et. al. describes a device that can be used to perform the underskin laser treatment of veins. The composition of the device described further limits the practicality of the invention. First, the device employs probes specially manufactured for the procedure, increasing the specificity of the equipment needed. Therefore, it may be difficult for users to have on hand all the various sized probes needed for different applications; and it may be costly for them to obtain additional attachments. Second, the special probes used in the treatment are too expensive to be disposed of; therefore they must be sterilized and sharpened after applications. This is both time consuming and cumbersome for the user. Time and effort are required to ensure that each probe is properly sterilized; and suitable sharpening depends on the care and skill of the user.

The method also requires multiple insertions of the device into the patient's skin. Each insertion must be made so that the probe is placed in close proximity to the vein being treated. The treated section of the vein is closed off, the device is removed, reinserted into another section of the vein, and the lazing procedure is repeated. This requirement makes the device more difficult to use. Further, by introducing multiple punctures of the skin the risk of infection is increased, as is the chance for disfiguration of the skin surface.

Therefore, a device that incorporates a standard, less costly and more readily available needle or probe would be beneficial. Further, there exist a vast number of subcutaneous aberrations to which underskin laser treatment may be applied. The aforementioned limitations prevent the device and method outlined in Trelles from being used.

The present invention is designed to employ standard, disposable needles of varying specifications by which to introduce any size laser carrying optical fiber required to a subcutaneous treatment site. The device and method may be used on all body structures that can be affected by laser treatment. Users may therefore apply treatment with the present invention on superficial as well as internal organs and tissues.

An aim of the present invention is to provide a device and method to safely and effectively treat underskin abnormalities through direct contact, without incurring the problems and deleterious side effects associated with the prior art.

OBJECTS AND SUMMARY OF THE INVENTION

It is an object of the present invention to address the need for an effective underskin laser treatment that can be used to eradicate internal abnormalities with greater specificity and minimal invasiveness.

It is a further object of the present invention to provide a device to deliver laser energy beneath the skin, with minimal insertions, directly into the treatment site, to either activate or inactivate that tissue, and to remedy the aberration.

It is yet another object of the present invention to provide a device that incorporates standard, inexpensive, and readily available insertion components, which make use of the device practical.

It is also an object of the present invention to provide a method by which the underskin laser treatments can be administered efficiently and in the least invasive manner.

Briefly stated, the present invention describes a device and method for underskin laser treatment that is minimally invasive, versatile and precise. The invention allows for underskin laser treatment with only minimal insertions into the area of treatment. For example, an entire area may be treated with one insertion. The invention incorporates a standard insertion component making the system inexpensive and easy for doctors to use. In addition, the invention allows users to get in direct contact with the treatment site, eliminating deleterious side effects encountered when treatment is administered to the skin surface. The invention has applications in several areas of treatment. First, underskin treatment of aesthetic skin blemishes such as sagging and wrinkles can be performed with minimal external effects. Laser power is delivered directly beneath the skin, bypassing harmful exposure of the skin surface to the radiation. Second, common vascular abnormalities such as capillary disorders, spider nevus, hemangioma, and varicose veins can be selectively eliminated. The device allows a simple, single insertion per treated structure and specific laser delivery. The needle is inserted into the vascular structure and any abnormalities are eradicated starting from the source and continuing through the entire structure. Third, when coupled with x-ray imaging, the present invention may be used to treat various internal body structures for example during surgery. X-ray imaging allows the user to orient the device within the body structures. Laser delivery treatment can then be administered as described above.

The above, and other objects, features and advantages of the present invention will become apparent from the following description read in conjunction with the accompanying drawings, in which like reference numbers in different drawings denote like items.

DETAILED DESCRIPTION OF THE PREFERRED EMBODIMENTS

Figure 1:
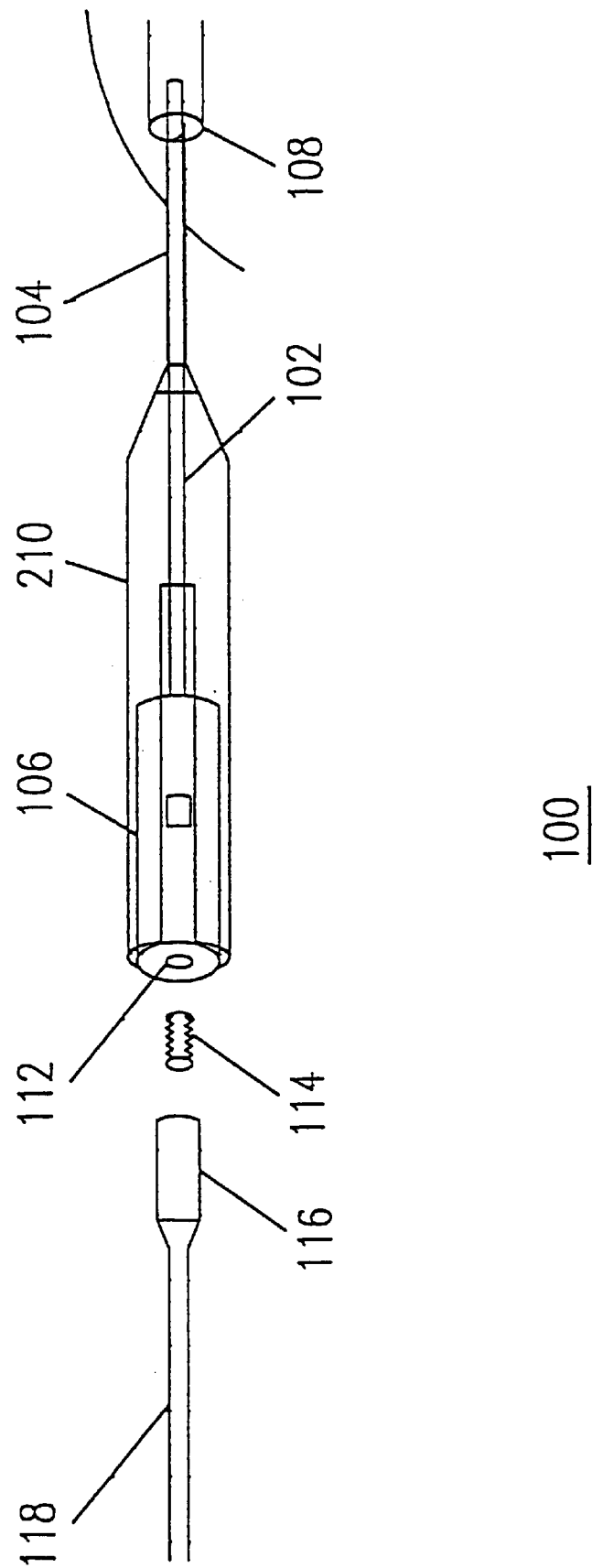
FIG. 1 shows an embodiment of the device that is used to introduce the laser fiber to the underskin treatment site.

The present invention describes a new device and method for the treatment of subcutaneous aberrations. Many conditions exist for which the proposed invention would apply. First, the device can be used in the eradication of wrinkles and in skin lifting/contraction procedures. Second, vascular aesthetic abnormalities can be corrected selectively. Third, the invention coupled with x-ray imaging can be applied to various internal body structures. Essentially, the device and method apply to all body structures that can be affected by laser treatment including superficial, subcutaneous structures, as well as internal organs and tissues. The versatility of the present invention makes it a beneficial, efficient and practical underskin laser treatment system for doctors to use.

The present invention allows the user to administer laser treatment to underskin sites without incurring skin surface damage commonly associated with such a procedure. For instance, wrinkle removal and skin lifting can be done without causing unnecessary skin surface scarring or redness. To administer the treatment of wrinkles for example, the hand piece of the device is used to introduce a needle containing the laser delivering optical fiber through the skin and into the selected underskin site. The needle is then retracted, the optical fiber is exposed, and laser energy is introduced into the tissue to be treated.

Similarly, vascular treatment involves only minimal insertions to introduce the laser-delivering fiber into the vascular structure. When treating vascular areas the user need only initially find the vessel that, once penetrated, will guide the placing of the fiber. In one pass, the user can effectively deliver a line of laser power to the internal areas of the vessel to cause scarring, coagulation or vaporization as desired. Effective treatment is achieved by introducing the optical fiber into the lumen of the specific vessel through the vessel wall. Lasing the blood contained in the vessel will induce a blood bubble explosion effectively damaging and coagulating the vessel wall and triggering a vein closing fibrosis. The target of all vascular treatments using the present invention is not the outside wall of the vessel, but the blood contents directly within the vessel.

The invention provides doctors with the option of using standard disposable needles with the device. Such needles are commonly used and commercially available making the system much more practical and economic than systems employing specially made probes. It is important to consider that a needle's sharpness is lost after one treatment application, and it must be re-sharpened or replaced. To adequately re-sharpen and sterilize a re-usable probe is difficult and time consuming for users. The use of disposable needles provides a safe, hygienic and economic alternative. With the invented device, the user might for instance change needle bore size when switching from the treatment of a vein to a capillary. The same user with the prior art would be required to obtain a specialized probe with dimensions small enough to fit into capillaries. The user may therefore, when administering treatment, choose to resterilize the standard needle along with the device's other components namely a hand piece and an extension component, or simply dispose of the needle and attach a replacement.

The device provides a unique advantage for users by allowing the orientation and position of the laser delivering optical fiber to be known during the treatment process without employing a special optical fiber. A metal-tipped fiber can be used in conjunction with x-ray imaging to show the position of the fiber in the treatment site. This limitation however, requires that a special metal-tipped optical fiber be used. The present invention solves this problem. The extension piece of the device maintains the optical fiber in a fixed position relative to, and at a fixed distance from, the device's hand piece allowing the user to know how much of the fiber has been inserted into the site.

The present device and method allows the treatment of a great number of areas within the human body that may be corrected with laser energy. Treatment can be administered under the visual control of the user when dealing with subcutaneous, superficial abnormalities; or under x-ray imaging when the site is deep within the body. The invention employs standard disposable needles making administering of the treatment less costly, quicker and more efficient for both the user and the patient.

FIG. 1 shows one preferred embodiment of device 100 displaying the insertion of the laser fiber into the treatment site. Standard bore needle 104 that can be of varying size depending on the application is inserted into the skin and directly into vascular structure 108. Laser delivery optical fiber 102 is inserted through device hollow channel of hand piece 110 and down through attached needle 104. Optical fiber 102 is affixed to hand piece extension 106 that slides within hand piece 110. Hand piece extension 106 allows the device user to maintain the position of laser fiber 102 when withdrawing needle 104 (method described in FIG. 2). Device 100 is attached to laser source through optical delivery fiber 118 that is lead into hand piece extension 106. In a disposable version of device 100, hand piece 110 can be detached from laser delivery fiber 118 and disposed. This variation requires that laser delivery fiber 118 terminates in plug structure 116 that corresponds to socket 112 in hand piece extension 106. When attaching hand piece 110 to laser delivery fiber 118, focusing lens stack 114 is placed into plug 116 before being inserted into socket 112.

Figure 2A:
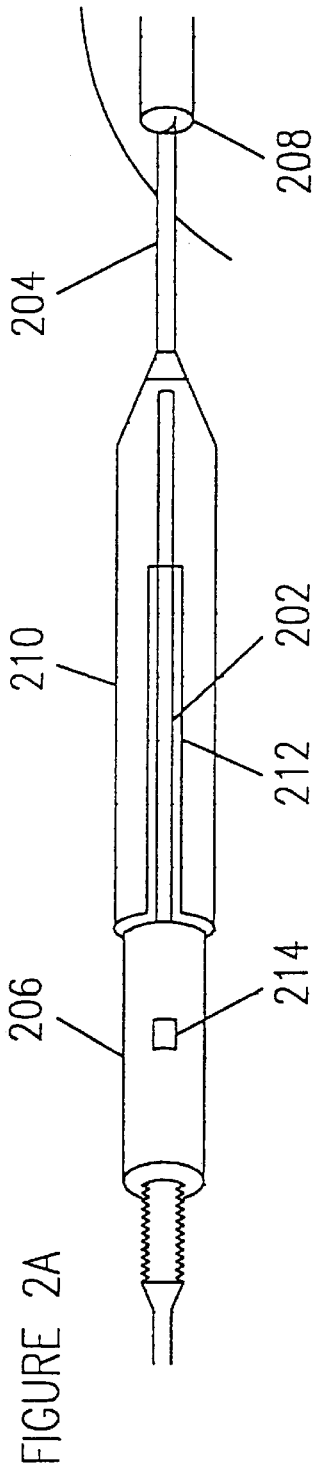
FIGS. 2A–2C show the method by which the needle and the fiber are inserted into the skin and the needle retracted exposing the fiber to the treatment area.
Figure 2B:
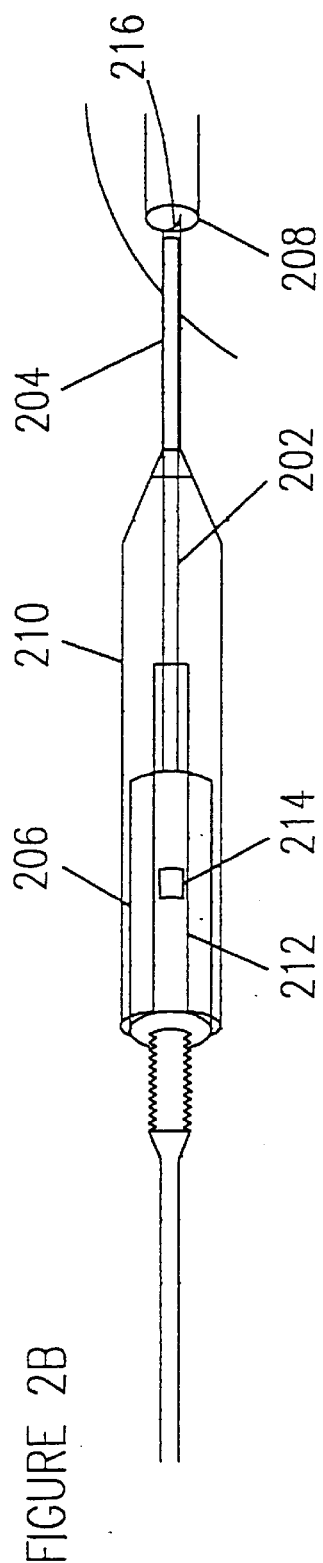
Figure 2C:
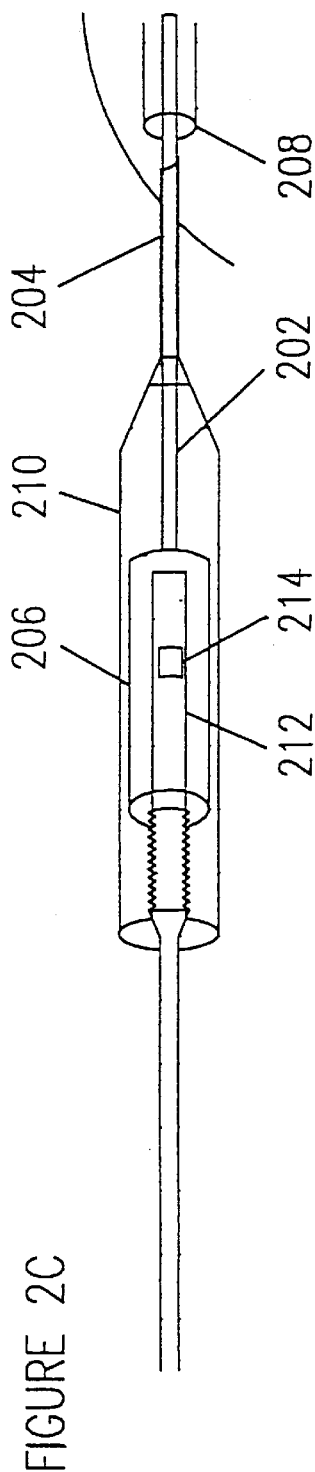

FIG. 2 shows a stepwise depiction of a method for use of the device. FIG. 2*a* shows standard sized needle 204 (needle size may be varied according to the application), attached to hand piece 210, being inserted through the skin and directly into desired vascular structure 208. Hand piece extension 206, that is affixed to laser delivery optical fiber 202 remains outset from hand piece 210. FIG. 2*b* shows hand piece extension 206 guiding laser delivery optical fiber 202 through hand piece 210 and into needle 204. Optical fiber 202 emerges from the distal end 216 of needle 204 and into vascular structure 208. Hand piece extension 206 has on its exterior, raised protrusion 214 that corresponds to groove 212 existing in hand piece 210. Protrusion 214 in conjunction with groove 212 allows user to maintain a desired orientation of optical fiber 202 during surgery. FIG. 2*c* shows hand piece 210 and attached needle 204 being retracted slightly from vascular structure 208. Hand piece extension 206 remains in the same position and therefore moves relative to retracting hand piece 210. Protrusion 214 slides in one dimension within groove 212 and thereby maintains optical fiber 202 in the same orientation. Optical fiber 202 along with hand piece extension 206 is advanced from hand piece 210 until protrusion 214 on hand piece extension 206 comes to the end of groove 212 in hand piece 210. Effectively, needle 204 and hand piece 210 are moved away from vascular structure 208 exposing optical fiber 202, through which laser radiation can be delivered. Optical fiber 202 can then be withdrawn via hand piece extension 206 back toward hand piece 210 and across the treatment area. In this manner, the amount of laser power delivered to optical fiber 202 and the speed at which optical fiber 202 is withdrawn into hand piece 210 can vary depending on the desired treatment being administered.

Following are examples of how the present invention might be used to treat various disorders. All the specifics described in each of the examples are only indicative of an exemplary treatment and it should be known that the parameters of the treatment could be altered depending upon the requirements of a specific application.

EXAMPLE 1

To treat wrinkles, use of the device creates a fibrosis below the wrinkles that will have a filling effect similar to a collagen insert. A laser flash to the reticular derma will create such a fibrosis (as part of the natural healing process). A 200-micron optical fiber is inserted into the hand piece fitted with a 25-gauge needle. The needle is inserted into the reticular derma directly under the wrinkle line. The laser power is set at 8–12 joules with both a working and idle time of 0.1 seconds. Three parallel treatment passes are made under the wrinkle lines in order to create a fibrosis larger than the wrinkle itself. Following the operation, no dressing is required, only moisturizing cream.

EXAMPLE 2

To obtain lifting or contracting of the skin, the device is inserted under the reticular derma or its lower border to induce a series of microscars. These microscars cause the reticular derma to contract. Contraction of the derma will tighten the skin surface.

If treatment is to be administered directly into the reticular derma then the device employs a 100-micron optical fiber used in conjunction with a 31-gauge needle. If treatment is administered on the lower border of the derma, a 200-micron fiber and a 25-gauge needle are used. In addition, for use in the lower border of the derma a special needle with a side-flashing fiber is needed. The laser output power is set at 3–5 joules with both a working and idle time of 0.2 seconds. These parameters may be varied according to the size, elasticity, and thickness of the skin treated.

The hand piece is extended, the optical fiber is placed inside the tip of the needle, and the needle is inserted into the thickness of the reticular derma. It is important to mark the area of treatment with a figure (e.g., a triangle illustrating the lateral jaw/neck angle—this will improve the effect of the lifting). The hand piece is then retracted to leave the tip of the fiber exposed to the reticular derma. In this manner, many continuous microcoagulated point lines are created, and the contraction of the skin is immediately evident. The contracted derma will relax to approximately 50–70% of its original elasticity.

In the case of very thin skin, to prevent burning or discoloration by flashing the skin superficially, the method is altered. The needle with the 200-micron fiber is positioned on the outside of the lower border of the reticular derma. The laser power is set at 3–7 joules with both a working and idle time of 0.3 seconds. Post-treatment, a cold compress is placed on the site for 15 minutes. Then compressive dressing is applied for 7 days.

Note: this process is different from skin resurfacing. In resurfacing, the treatment acts on the surface of the skin, causing contraction through heat absorbed by the reticular derma after the vaporization of the corneum and papillary derma. The present invention, by inserting the fiber directly into the reticular derma or in its lower border, activates the same mechanism of contraction, but without any affect on the outside skin surface. This treatment applies to the lifting of the face, and lifting of the skin in general.

EXAMPLE 3

The invention describes a method for use of the device to treat abnormal capillaries. The treatment involves the delivery of laser power to the site to inactivate the desired capillary structure. The device specifications vary depending on the size of the capillary being treated. For treatment of capillaries 0.3–1 mm in size a 200-micron optical fiber is inserted into a hand piece fitted with a 25-gauge needle. For a capillary less than 0.3 mm in size, the set up is altered to employ a 100-micron fiber and a 31-gauge needle.

The power output of the laser is set to continuous pulse mode if treating capillaries of a superficial branch, and to single pulse mode if treating a feeding vein. When set to continuous pulse mode, the laser output will have both a working and idle time of 0.3 seconds. When set to single pulse the output will have a working time of 0.3 seconds. These parameters may vary a little depending on the thickness of the vessel wall.

There is usually one feeding vein for a number of superficial capillary branches. The treatment method functions by cutting off the upstream-most source and then systematically progressing downstream. Therefore, to begin treatment, the feeder vein must be located and treated first.

Prior to insertion of the device and depending on the consciousness of the patient, a superficial anesthesia such as a cream containing xylocaine may be applied to the treatment site.

Following this, the hand piece extension is drawn out placing the optical fiber just inside the tip of the needle so that the needle can enter the skin without any obstructions. When the tip of the needle has reached the feeding vein, the hand piece extension is retracted and the tip of the optical fiber enters the vessel. The retraction ensures that the energy of the laser will not be directed at the needle, which may destroy the fiber, but will focus directly on the wall of the feeding vessel and the blood contained therein. The laser power required is as follows: for capillaries greater than 0.3 mm in diameter the power output is 5–6 joules. If the capillary is less than 0.3 mm in diameter, then the power output drops to 3–4 joules.

After treatment of the vein is complete, the laser is shut off and the fiber is retracted. Generally the device is reinserted 2 or 3 more times, one insertion per treatment structure, in order to coagulate all the feeding vein and the immediate border tissue. For example, one insertion is required for treatment of the feeder vein, one for the capillary bed and so on. In this manner, the resulting scaring will definitely close the connection between the feeding vein and the visible superficial branches.

The superficial branches are then treated as follows: the device, with the extension out and the fiber inside the needle, is inserted inside the capillary branch. The laser power is changed to continuous pulse mode. Retracting of the extension places the optical fiber in direct contact with the lumen of the capillary vessel. The capillary branch is coagulated by retraction of the needle and activation of the laser. The optical fiber can be slowly retracted along the treatment area to effectively create a continuous coagulation-point line. After treatment, the site is dressed with a compressive bandage or stocking.

EXAMPLE 4

To treat spider veins, a 200-micron optical fiber is inserted in the hand piece that is fitted with a 25-gauge needle. The needle is inserted in the feeding vein of the spider nevus. The laser energy is set on single pulse mode with a working time of 0.3 seconds and output power of 5 joules. The hand piece is then retracted to allow the tip of the fiber to be exposed to the inside of the feeding vein [and the spider nevus]. The laser is flashed 4–5 times within the vein and on its walls. The flash will close the nevus through coagulation and microexplosion. Additional scarring will ensure that the vein is closed indefinitely.

EXAMPLE 5

In the treatment of varicose veins, the size of the optical fiber used will vary depending on the diameter of the vein to be treated. To treat veins up to 3 or 4 mm in size, a 400-micron optical fiber is inserted into the hand piece that is fitted with a 21-gauge needle. For veins greater than 4 mm a 600-micron fiber is used in conjunction with an 18-gauge needle.

The laser is set on continuous pulse mode with a working time of 0.3 seconds and an idle time of 0.3 seconds. The laser output power would need to be varied depending on the vein diameter: for a vein less than 4 mm in diameter, 7–10 joules of power is needed; for veins greater than 4 mm in diameter, 12–15 joules are needed.

To administer treatment, the area first should be marked with a dermographic pen to indicate abnormal portions of the vein identified from prior examinations. Local anesthetic containing xylocaine or a similar compound is then applied along the marked line of treatment. Next, the course of the vein is detected and treated as follows: the hand piece extension is retracted and the optical fiber is placed inside the needle just behind the tip. The needle is then inserted into the vein and the laser is set to single pulse mode. The hand piece is retracted in order to expose the tip of the fiber to the lumen of the vein. Laser power is then administered: a series of 10–15 flashes are sufficient to create a scar that closes off the vein. Next, the laser setting is changed to continuous pulse mode. The needle is then inserted into the vein along the length of the marked line, spanning the entire treatment length. The hand piece is retracted and the optical fiber is free to flash the inside wall of the vein and its blood contents. A continuous coagulation line is created inside the vein. The laser flash specially effects the blood by creating a micro bubble explosion destroying the vein, which, when healing will form a thin fibrosis later to be absorbed.

EXAMPLE 6

The device may be coupled with x-ray imaging to perform surgery on various internal body structures. The x-ray imaging will allow the user to determine the placement of the metal needle in the body structure. In addition, the user might vary the size and length of the insertion needle to apply the device to different neuro-surgical procedures or to enable the user to perform operations on body organs where vaporization or coagulation is required.

Having described preferred embodiments of the invention with reference to the accompanying drawings, it is to be understood that the invention is not limited to the precise embodiments, and that various changes and modifications may be effected therein by one skilled in the art without departing from the scope or spirit of the invention as defined in the appended claims.

What is claimed is:

1. An underskin laser treatment device for the treatment of skin irregularities, elimination of vascular abnormalities and general assistance in surgical procedures comprising:

an optical fiber having a proximal and a distal end;

said optical fiber being attached at its proximal end to a laser power source;

a hand piece fitted with a standard insertion needle, said hand piece having a hollow channel within its body and having a proximal and a distal end;

an extension which can fit within said hollow channel and which has means for passing said optical fiber through said extension and said hand piece into said insertion needle;

said extension having a protrusion which is keyed to a groove within said hand piece's channel wall for guiding said fiber's motion through said hand piece and said insertion needle; and wherein said optical fiber is attached to said extension on said proximal side of said hand piece such that upon engaging said extension into said channel of said hand piece said distal end of said optical fiber terminates within said distal end of said needle.

2. An underskin laser treatment device according to claim 1, wherein said insertion needle is retractable after insertion to expose a section of said optical fiber.

3. An underskin laser treatment device according to claim 1, wherein said groove in said hand piece has a length such that when said extension's protrusion mates with said groove and is advanced forward to said distal end of said hand piece said attached optical fiber extends in a treatment site a distance chosen for treating in one application.

4. An underskin laser treatment device according to claim 1, wherein said insertion needle is a sterile, disposable needle.

5. An underskin laser treatment device according to claim 1, wherein said hand piece, and said extension are each capable of repeated resterilization without compromising their performance.

6. An underskin laser treatment device according to claim 1, wherein said insertion needle is capable of resterilization.

7. A method for underskin laser treatments using a treatment device as described in claim 1, comprising the steps of:

a. fitting the hand piece with an insertion needle of bore size selected to provide passage of the optical fiber, having a diameter required by treatment specifics;

b. attaching said optical fiber to the extension at a distance from said fiber's distal end to permit extension of said optical fiber beyond said insertion needle into a selected treatment site;

c. inserting said optical fiber with attached extension into said hand piece and aligning said extension with said hand piece so that a protrusion on said extension fits into a groove within a channel wall of said hand piece;

d. inserting said needle through a patient's skin into said selected treatment site;

e. exposing said distal end of said optical fiber within said selected treatment site;

f. activating a laser power source attached to a proximal end of said optical fiber and delivering laser energy to said treatment site while moving said extension along said hand piece's groove towards said hand piece's proximal end and withdrawing said optical fiber distal end back towards said needle's distal tip, thus allowing specific treatment of desired structures with a minimal number of insertions; and g. wherein withdrawal speed and laser energy deposited is controlled to achieve desired treatments.

8. A method for underskin laser treatments according to claim 7, wherein said exposing said distal end of said optical fiber within said selected treatment site is advancing said distal end of said optical fiber within said treatment site by sliding said extension into said hand piece until said extension's protrusion engages the distal end of the groove within said hand piece.

9. A method for underskin laser treatments according to claim 7, wherein said exposing said distal end of said optical fiber within said selected treatment site is retracting said insertion needle to expose said distal end of said optical fiber.

10. A method for underskin laser treatments according to claim 7, wherein for superficial treatments step d. further comprises the step of:

after needle insertion, guiding insertion of said optical fiber into said selected treatment site by visual control externally to a patient body.

11. A method for underskin laser treatments according to claim 7, wherein for treatment of inner body structures step d. further comprises the step of:

after needle insertion, guiding insertion of said optical fiber into said selected treatment site by x-ray imaging of said needle's distal tip.

12. A method for underskin laser treatments according to claim 7, wherein said desired treatments include coagulation of blood, micro explosion of blood within a blood vessel and micro scarring of tissue.

* * * * *